(12) United States Patent
Lapidot et al.

(10) Patent No.: US 12,396,597 B2
(45) Date of Patent: Aug. 26, 2025

(54) FOOD STORING AND CONSUMPTION TRACKING SYSTEM AND METHOD

(71) Applicants: Tal Lapidot, Tel Aviv (IL); Daniel Sorkin, Tel Aviv (IL); Amir Ben-Ari, Tel Aviv (IL); Itai Harpaz, Tel Aviv (IL); Guy Gutfarb, Tel Aviv (IL); Ofer Baratz, Tel Aviv (IL)

(72) Inventors: Tal Lapidot, Tel Aviv (IL); Daniel Sorkin, Tel Aviv (IL); Amir Ben-Ari, Tel Aviv (IL); Itai Harpaz, Tel Aviv (IL); Guy Gutfarb, Tel Aviv (IL); Ofer Baratz, Tel Aviv (IL)

( * ) Notice: Subject to any disclaimer, the term of this patent is extended or adjusted under 35 U.S.C. 154(b) by 0 days.

(21) Appl. No.: 18/885,984

(22) Filed: Sep. 16, 2024

(65) Prior Publication Data

US 2025/0009185 A1 Jan. 9, 2025

Related U.S. Application Data

(63) Continuation of application No. 17/283,189, filed on Apr. 6, 2021, now Pat. No. 12,102,269.

(51) Int. Cl.
*A47J 47/10* (2006.01)
*B65B 31/02* (2006.01)
(Continued)

(52) U.S. Cl.
CPC ............ *A47J 47/10* (2013.01); *B65B 31/028* (2013.01); *B65D 81/2015* (2013.01); *G01N 33/02* (2013.01)

(58) Field of Classification Search
CPC ........ A47J 47/10; B65B 31/028; B65B 61/26; B65B 63/005; B65B 57/00; B65D 81/2015; B65D 81/2038; G01N 33/02
See application file for complete search history.

(56) References Cited

U.S. PATENT DOCUMENTS 6,256,905 B1 7/2001 White
9,352,864 B2 * 5/2016 Hammad .............. B65B 31/024
(Continued)

FOREIGN PATENT DOCUMENTS

CN 201604908 U 10/2010
KR 101809224 B1 1/2018
(Continued)

OTHER PUBLICATIONS

IP Australia, Westhuizen, Marthinus, Examination report No. 1 (Aug. 8, 2024), Chatswood, AU.
(Continued)

*Primary Examiner* — Joshua E Rodden
(74) *Attorney, Agent, or Firm* — Martin IP Law Group; C. Richard Martin

(57) ABSTRACT

Food storing and tracking method and system including plurality of food containers, plurality of sealing lids, a registry, and a base unit including a weight measurer, a reader, an interface and a processor. Food item inserted into food container comprising unique identifier. Food container placed onto base unit and releasably sealed with complementary sealing lid upon engagement with base unit. Interface tags food item of food container. Reader identifies food container by reading unique identifier. Weight measurer measures weight of food container. Weight of food item calculated by subtracting known weight of food container or container type from measured weight, and calculated weight logged. Registry updated with information relating to food container and contents thereof. A freshness of food item in food container is tracked, based on projected shelf life information for potential stored food items, and based on updated registry information, and alert relating to tracked freshness is generated.

13 Claims, 4 Drawing Sheets

(51) Int. Cl.
*B65D 81/20* (2006.01)
*G01N 33/02* (2006.01)

(56) References Cited

U.S. PATENT DOCUMENTS

| | | | |
|---|---|---|---|
| 10,546,266 B1 | 1/2020 | Bose | |
| 10,562,690 B2* | 2/2020 | Plazarte | B65D 51/1683 |
| 10,759,588 B1 | 9/2020 | Lobisser et al. | |
| 11,603,251 B2* | 3/2023 | Bamonte | B65B 31/02 |
| 11,845,601 B2* | 12/2023 | Clair | B65D 81/2038 |
| 2003/0182900 A1 | 10/2003 | Bowden et al. | |
| 2016/0243850 A1 | 8/2016 | Phillips et al. | |
| 2018/0141738 A1 | 5/2018 | Armano et al. | |
| 2018/0249735 A1* | 9/2018 | Espinosa | G06Q 10/083 |
| 2019/0069728 A1* | 3/2019 | Alfarra | A23L 5/30 |
| 2021/0163165 A1 | 6/2021 | Lobisser et al. | |
| 2022/0000318 A1* | 1/2022 | Lapidot | A47J 47/10 |
| 2022/0415496 A1* | 12/2022 | Levy | G16H 20/13 |
| 2023/0316032 A1* | 10/2023 | Rigby | G01N 27/041 235/492 |
| 2023/0391488 A1* | 12/2023 | Shtraks | B65D 5/48014 |

FOREIGN PATENT DOCUMENTS

| | | |
|---|---|---|
| WO | 9500030 A1 | 1/1995 |
| WO | 2017087983 A1 | 5/2017 |
| WO | 2017158591 A1 | 9/2017 |

OTHER PUBLICATIONS

European Patent Office, Supplementary Search Report, (Jun. 17, 2022), Munich, DE.
European Patent Office, European Search Opinion, (Jun. 17, 2022), Munich, DE.

* cited by examiner

FOOD STORING AND CONSUMPTION TRACKING SYSTEM AND METHOD

BACKGROUND OF THE INVENTION

Field of the Invention

The present invention generally relates to food storage and in particular to vacuum food storage.

Description of the Related Art

Food waste is a global issue, with nearly a third of all food grown eventually ending up wasted, wherein nearly half of that waste occurring at the consumer level. Greater awareness in recent years has led to various attempts to reduce food waste and research into why consumers waste food. Leading reasons for food waste appear as over-stocking, uncertainty of freshness (throwing out food that is still fine for consumption), bad inventory management (consuming long shelf life items while other items are about to expire), and a lack of knowledge on best storage practices (e.g., cucumbers should be dried before storage and optimally wrapped individually by an absorbent paper).

While there have been attempts to create food inventory systems (for example U.S. Pat. No. 5,487,276), such systems have focused on simply tracking inflow of food and how long it has been in storage. So far, such systems do not appear to have been successful in substantially changing waste habits or reaching meaningful market adoption.

The description above is presented as a general overview of related art in this field and should not be construed as an admission that any of the information it contains constitutes prior art against the present patent application.

SUMMARY OF THE INVENTION

This summary is provided to introduce a selection of concepts in a simplified form that are further described below in the detailed description.

This summary is not intended to identify key features or essential features of the claimed subject matter, nor is it intended to be used to limit the scope of the claimed subject matter.

According to one aspect, the system features food item storing and tracking system having at least one food container, at least one sealing lid, each complementary to one of said at least one container, a vacuum seal inducer, and sensor(s) for measuring freshness of the food item. The system is configured to allow placing the food item in the container, releasably sealing the at least one container with the sealing lid complementary thereto, subjecting the sealed container to sub atmospheric pressure by employing the vacuum seal inducer on the sealed container, and tracking the freshness of the food item with the sensor(s) for measuring freshness.

In accordance with another aspect there is provided a food storing and consumption tracking system. The system includes a base unit, at least one container, at least one sealing lid complementary to at least one of the at least one container, and an identifier unique to each of the at least one container and/or at least one lid.

By "complementary" we refer to a sealing lid and a container each having features, such as size and contours, closely matching features of the counterpart.

A container when detached from a sealing lid may be exposed to the environment outside the container. When the container is attached to a complementary sealing container the container may become isolated from the environment outside the container.

Each system is configured to allow releasable sealing of the at least one sealable container, only upon engagement of the respective at least one container and/or sealing lid with the base unit. The system may be further configured to allow opening i.e., unsealing, of at least one container.

In some embodiments the at least one container and/or sealing lid is particularly adapted, i.e., includes at least one physical feature such as shape, that allows for their engagement with the base unit. In other words, commercially available containers and/or sealing lids may not be engageable with the base unit, at least not such as to seal the containers solely as a result of the engagement.

The system may be configured to allow releasably sealing the at least one sealable container upon the engagement with at least one sealing lid, in conjunction with reading the unique identifier and optionally measuring of the content of the respective container. In some embodiments the system is further configured to allow at least one of the following operations: recording, tracking, and presenting relevant information derived by measuring at least one sealable container, wherein the system is used for food storing and for consumption tracking.

In some embodiments the system comprises a plurality of containers.

The base unit may include at least one of:

1. a weight measurer capable of measuring the weight of each at least one container placed thereon, both when empty and when containing a foodstuff;
2. a data processing device capable of at least one of the following: updating a registry of containers and their inputted content, calculating the weight of the content, and logging weight and other collected data including the timestamp of the event;
3. a reader for identifying at least one container and/or at least one lid and capable of reading a unique identifier for at least one container or sealing lid, when a container or lid is placed on the base unit;
4. a vacuum seal inducer for essentially vacuum sealing the at least one container, when the sealable container and/or a complementary sealing lid engages the base unit;
5. a connectivity module allowing the system to connect and update an external service holding the registry and additional data such as old information about the container prior to removing and/or adding food item/s therein, and new information after adding new food items therein;
6. a local memory device capable of storing a registry of containers and their inputted contents, and/or information on projected shelf life for potential stored food items; and
7. an interface allowing users to tag the content of a container when changed.
8. Sensor(s) for measuring freshness of the food.

Note that "placed on" the base unit in some embodiments comprises placing against the base unit from below of sideways, for example in some embodiment a sealing lid may be brought from below the "base unit" and then pushed upwards against the base unit.

In accordance with another aspect there is provided a food storing and consumption tracking method including:
1. providing at least one container, at least one complementary sealing lid, and sensor(s) for measuring freshness of the food items; placing the food in one of the at least one container, wherein each at least one sealable container is associated with a unique identifier;
2. providing a base unit and releasably sealing one of the at least one container with a complementary sealing lid, only upon engagement of the sealable container with the base unit;
3. sealing the container when closed by the complementary sealing lid and engaged with the base unit, in conjunction with reading the unique identifier associated with the container, and measuring the content of the sealable container; and
4. recording, tracking, and presenting the relevant information respective of the sealable container based on measuring or the content, sensing freshness, and/or user tagging, for example a reference name or number ascribed to the container by the user.

According to another aspect, a food storing and tracking system is provided, comprising:
at least one food container;
at least one sealing lid, each complementary to one of said at least one container;
a vacuum seal inducer; and
sensor(s) for measuring freshness of the food item;
wherein the system is configured to allow:
placing the food item in the container;
releasably sealing the at least one container with the sealing lid complementary thereto;
subjecting the sealed container to sub atmospheric pressure by employing the vacuum seal inducer on the sealed container; and
tracking the freshness of the food item with sensor(s) for measuring freshness.

Some system embodiments further comprise:
a base unit;
wherein only upon engaging the at least one container or the at least one sealing lid associated therewith, with the base unit, the at least one container is releasably sealed with the sealing lid complementary thereto.

Some system embodiments further comprise at least one unique identifier, each associated with one of the at least one container, and/or one sealing lid complementary thereto; wherein the system is further configured to allow reading the at least one unique identifier.

In some system embodiments only upon engaging a container or sealing lid associated therewith with the base unit, the container is opened.

In some system embodiments the system is configured to allow releasably sealing one of the at least one sealable container only upon engaging the container or sealing lid associated therewith with the base unit, in conjunction with reading the unique identifier.

In some system embodiments the system is further configured to allow weighing the at least one container having the food item placed therein.

In some system embodiments the tracking comprises recording and presenting data related to the freshness measurements.

In some system embodiments the base unit comprises at least one of the following:
a weight measurer for measuring the weight of the at least container placed thereon;
a processor operational for updating a registry of containers and their inputted food item, calculating the weight of the food item, and logging weight and a timestamp of the event;
a reader for identifying at least one container and/or sealing lid, capable of reading a unique identifier when a container and/or sealing lid is placed against the base unit.

In some system embodiments the base unit further comprises at least one of:
a connectivity module allowing the system to connect and update an external service holding data comprising the unique identifier and freshness measurements;
a local memory capable of holding a registry of containers and their inputted contents, and/or information on projected shelf life for potential stored food items; and
an interface allowing tagging the food item placed in one of the at least one container.

In some embodiments the sensor(s) comprise at least one of:
a. aerosol particle counters that work on the principal of light scattering or light blocking;
b. optical/electromagnetic (EM) radiation sensors, operational to detect any EM radiation at wavelength suitable range that detect visual image al;
c. optical/electromagnetic (EM) radiation sensors, operational to detect any EM radiation at wavelength suitable range that detect the presence or particular wavelength composition of emitted/reflected/transmitted EM radiation;
d. sensors that include active transmitters of such radiation, which detect scattering/blocking of that light;
e. gas sensors sensitive to carbon dioxide, and/or ethylene and/or biogenic amines and/or other gases and/or volatile organic compounds released by maturing or rotten food or released during bacterial and fungal proliferation;
f. carbon nanotubes, through which an electric current changes in the presence of a particular gas, which is a decay marker;
g. polymer material that raises a "red flag" by changing color in the presence biogenic amines; and
h. pH-sensitive sensors for indicating the presence of particular gases and/or volatile organic compounds.

In some system embodiments the sensor(s) operate or are disposed according to at least one of the following:
a. installed in the sealable container;
b. installed in the lid;
c. installed in base unit;
d. operational to detect EM presence or image through a wall of the container or the lid, wherein the wall is transparent to the relevant detectable wavelengths;
e. operate when the lid is open to allow direct exposure to and interaction with the exposed contents;
f. exposed to air extracted from the container in the course of air removal for inducing of sub-atmospheric pressure in the container;
g. located in the extraction path in the may be disposed in base unit; and independent units physically separate from other components of the system, operational for independently detecting extent of freshness and which are enabled to communicate for transmitting the readings detected by the sensors.

According to another aspect, a method for storing and tracking food items is provided, the method comprising:
providing at least one food container, at least one sealing lid, each lid complementary to one of said at least one container, and sensor(s) for measuring freshness of the food items;
placing at least one food item in one of the at least one container;

releasably sealing the container with the sealing lid complementary thereto;

subjecting the sealed container to sub-atmospheric pressure, and tracking the freshness of the food item with sensor(s) for measuring freshness.

Some method embodiments comprise assigning a unique identifier to each of the at least one container and/or complementary lid, wherein the one container is sealed by a base unit, when closed with the complementary sealing lid and when the one container and/or the complementary sealing lid are placed against the base unit, in conjunction with reading the assigned unique identifier and measuring a content of the one container.

In some method embodiments the sealing occurs only upon engaging the one container and/or complementary lid with the base unit.

Some method embodiments further comprise one or more of: recording, tracking, and/or presenting information respective of the one container, wherein the information is based on the measuring of the content, sensing freshness, and/or user tagging in addition or in lieu of the measuring.

BRIEF DESCRIPTION OF THE DRAWINGS

The present invention will be understood and appreciated more fully from the following detailed description taken in conjunction with the drawings in which.

Figure 1:
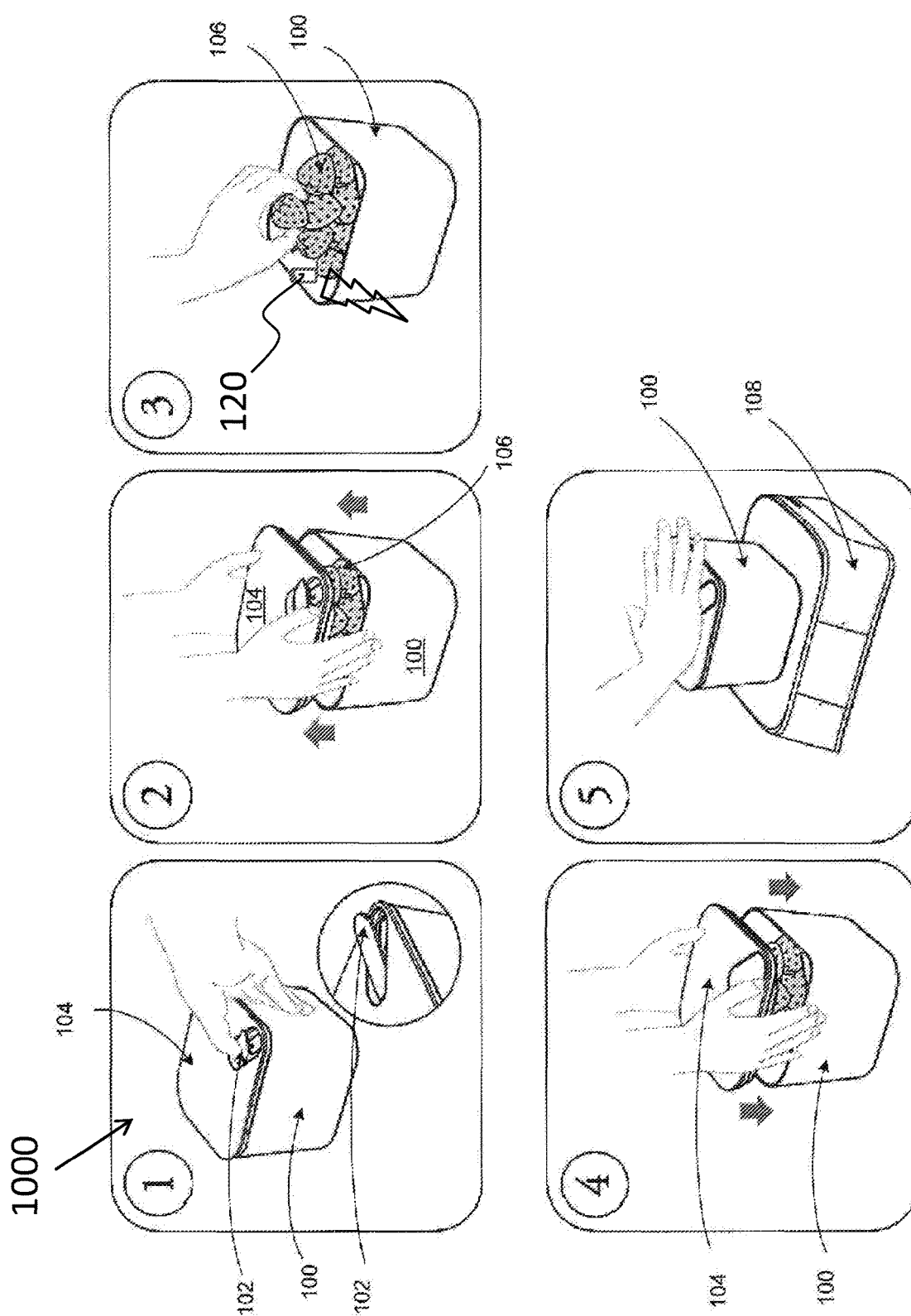
FIG. 1 shows an embodiment that Illustrates different stages of use of the system.

The figures illustrate generally, by way of example, but not by way of limitation, various embodiments discussed in the present document.

For simplicity and clarity of illustration, elements shown in the figures have not necessarily been drawn to scale. For example, the dimensions of some of the elements may be exaggerated relative to other elements for clarity of presentation. Furthermore, reference numerals may be repeated among the figures to indicate corresponding or analogous elements. The figures are listed below.

The number of elements shown in the Figures should not be construed as limiting, and is for illustrative purposes only.

DETAILED DESCRIPTION OF THE EMBODIMENTS

According to one aspect, there is provided a perishable food inventory management system having a base unit capable of measuring weight, identifying specific sealable containers and sealing the sealable containers when placed there on. The system further includes complementary sealable containers featuring unique identifiers that can be sealed only upon placement on the base unit. Sealable containers may refer as examples to a box with an attached or removable lid, or to a resealable re-usable bag.

The system records data respective of food items within the sealable containers, namely consumption data, based on measurements collected upon each sealing, forcing user compliance by requiring to place sealable containers on the base unit between uses. Sealing, identification, and measuring are synergistically performed whenever the user needs to seal the sealable container, by taking advantage of the mere placement of the sealable container over a base unit for the sealing procedure. The collected data can be used for inventory management and combined with additional features to provide expiration date tracking and management.

When a user inserts food in one of the system sealable containers, the user is then required to place the filled sealable container on a base unit for sealing the sealable container. The base unit collects data, including the identification of the sealable container and the net weight of its contents, and records such data in a registry.

Each time a user reseals a sealable container (e.g., after opening and optionally consuming some of the contained food) such data is added to the registry, to thereby allow consumption tracking.

Reference is now made to FIG. 1 which is an embodiment that illustrates different stages of use of the system 1000. In slide (1) sealable container 100 is unsealed by pressing release handle 102 of complementary sealing lid 104 (this step is skipped if the sealable container is already unsealed). In this illustration this is achieved by releasing the negative pressure in the sealable container 100. In slide (2) complementary sealing lid 104 is detached from sealable container 100. In slide (3) food 106 is taken from (or placed in) sealable container 100. In slide (4) complementary sealing lid 104 is placed back on sealable container 100. In slide (5) sealable container 100 is placed on base unit 108 for sealing/resealing (in this illustration this is achieved by generating negative pressure inside sealable container 100.

The system 1000 combines tracking of inflow with consumption tracking and information stored in remote servers 130 (see FIG. 3) or locally, to provide users with the information required for improving their storage practices and align their purchasing with their consumption. Furthermore, the system 1000 encourages users to track their consumption by allowing sealing of the sealable containers 100 only when interfaced with a base unit 108 which measures the current weight of the contents and updates the system's registry of stored contents, to thereby create compliance and solve a repeating problem entailed with such sealing systems. Access to consumption data may allow users to better match purchase with actual consumption habits, and the creation of a centralized inventory which may allow users to discern which items are closest to expiration of shelf life and thereby encourage better inventory management. Embodiments may also include additional means for measuring freshness of the food item, comprising sensor(s) 120 (FIG. 1 slide 3) capable of detecting, metering, measuring, and/or tracking rot or decay of contents. For example, sensors 120 can include sensors such as aerosol particle counters that work on the principal of either light scattering or light blocking, from the stored food items and/or air inside the containers, e.g., optical/electromagnetic (EM) sensors, operational to detect any EM radiation at wavelength suitable range/s) that detect visual image that may be analyzed, or detect the presence or particular wavelength composition of emitted/reflected/transmitted EM light, including light originating from active transmission of such radiation, that can be associated with the extent of freshness or rot of the food. Sensors 120 can include as another example sensors such as gas sensors or indicators sensitive to gases released by maturing or rotten food which can be found to be decaying food markers or characteristic volatile organic compounds released during bacterial and fungal proliferation, such as carbon dioxide and/or ethylene and/or biogenic amines (e.g., sensors featuring carbon nanotubes through which an electric current changes in the presence of a particular gas which is a decay marker, or polymer material that raises a "red flag" by changing color in the presence of biogenic amines). In a further example, sensors 120 can include sensors such as pH-sensitive sensors or indicators (that can sense for example the release of carbon dioxide via measurement of a liquid absorbing the gas). Accordingly, sensors 120, which may include any and all of the above mentioned sensor types provide information on best storage practices, to help people and businesses to further decrease food waste. Sensor(s) 120 may be installed in sealable container 100. In other embodiments sensors similar to sensor(s) 120 may be installed in lid 104. In further embodiments sensor(s) similar to some of sensor(s) 120 may be installed in base unit 108, and operational to detect EM presence or image through a wall of container 100 or lid 104, wherein the wall is transparent to the relevant detectable wavelengths, or to operate when lid 108 is open to allow direct exposure and interaction of the sensor(s) with the exposed contents, or exposed to air extracted from the container in the course of air removal for the induction of sub-atmospheric pressure in container 100. In particular freshness sensors located in the extraction path, may be disposed in base unit 108, with readily available power supply and connection to the data gathering components in base unit 108. while taking synergetic advantage of the coupling of container 108 for the purpose of air removal. In further embodiments, such sensor(s) include independent units physically separate from other components of system 1000, operational for independently detecting extent of freshness (e.g., when container 100 is opened), and which are enabled to communicate with the base unit 108 (or with other communication means) for transmitting the readings detected by the sensors for further processing. Sensors which are disposed in container 100 or lid 104 may be powered by properly sealed electric battery source (which may be replaceable and/or rechargeable, including by physical direct wired connection or wireless induction charger disposed in or to base unit 108 or to a separate charger (that may be placed in the refrigerator).

Tracking of the detected, metered or measured information is either presented by the sensors (when enable to display such information) or relayed to other components of the system which store the information and/or process the findings, and/or present the information.

According to one aspect three components are combined, namely-sealable containers, complementary sealing lids, and a base unit, which operate as further elaborated below:
1. Sealable containers: Each sealable container is marked such that the base unit can distinguish between the sealable containers, by integration of a unique identifier into the sealable container, such as: an RFID; b) an optical sign (such as a number or a barcode); c) an alternative physical marker (such as special grooves or etchings), wherein the base unit is equipped with an appropriate reader which is operational for identifying the specific sealable container by reading the unique identifier; or d) any combination of the above
2. Complementary sealing lids: A complementary sealing lid, for each of the sealable containers, allows sealing the sealable containers, only upon engagement of the sealable containers with the base unit.

An example that may be achieved is through combination with the system described in international patent application No. PCT/IL2017/050313, international application publication no. WO-2017/158591 A1 (herein below-"'591"), allowing the creation of sub-atmospheric pressure within the sealable container and sealing thereof. '591 describes a vacuum container and a system which includes a complementary base, including a three-part airway, a sealing lid, and a lid release button. The three-part airway features an internal air chamber, an extraction airway, and a one-way check-valve preventing ambient air from penetrating the internal air chamber through the extraction airway when vacuum sealed. The extraction airway extends between the top and the bottom of the container and includes an internal air extraction outlet, disposed at the top of and within the internal air chamber, and an external air extraction outlet outside the container, disposed at the bottom of the container, and configured to be coupled to an external air pump.

In another similar example from '591, a vacuum container for providing vacuum sealing thereof is provided, including:
1. a three-part airway comprising:
   a. an internal air chamber for containing products and fluids;
   b. an extraction airway extending between the top and the bottom of the container, for allowing extraction of air from said internal air chamber; said extraction airway comprising:
      i. an internal air extraction outlet, disposed at the top of and within said internal air chamber; and
      ii. an external air extraction outlet outside said container, disposed at the bottom of said container, configured to be coupled to an external air pump for extracting air from said container; and
   c. a one-way check-valve disposed in said extraction airway and separating an internal airway portion and an external airway portion of said extraction airway, for preventing ambient air from penetrating said internal air chamber through said extraction airway when vacuum sealed, and allowing passage of air when pressure is equalized in said internal airway portion and said internal air chamber;
2. a lid fitted to sealingly cover said internal air chamber, wherein said internal air extraction outlet is disposed at one of: said lid; and the side wall of said internal air chamber; and
3. a lid-release button allowing for selected equalization of pressure within said covered internal air chamber for allowing release of said lid under pressurized container conditions.

In another similar example from '591, a vacuum container system for providing vacuum sealing of containers is provided and includes:
1. a vacuum container comprising:
   a. a three-part airway comprising:
      i. an internal air chamber for containing products and fluids;
      ii. an extraction airway extending between the top and the bottom of the container, for allowing extraction of air from said internal air chamber; said extraction airway comprising:
         a. an internal air extraction outlet, disposed at the top of and within said internal air chamber; and
         b. an external air extraction outlet outside said container, disposed at the bottom of said container, configured to be coupled to an external air pump for extracting air from said container; and
         iii. a one-way check-valve disposed in said extraction airway and separating an internal airway portion and an external airway portion of said extraction airway, for preventing ambient air from penetrating said internal air chamber through said extraction airway when vacuum sealed, and allowing passage of air when pressure is equalized in said internal airway portion and said internal air chamber;

b. a lid fitted to sealingly cover said internal air chamber, wherein said internal air extraction outlet is disposed at one of: said lid; and the side wall of said internal air chamber; and c. a lid-release button allowing for selected equalization of pressure within said covered internal air chamber for allowing release of said lid under pressurized container conditions; and 2. a vacuum base comprising an external air pump connectable to said external air outlet for extracting air from said container when sealingly covered by said lid.

Some of the vacuum container systems as described in '591 may further comprise:

a centering disk;

a connection sensor detecting when said vacuum container and said vacuum base are coupled; and a suction port coupling said extraction airway of said vacuum container with said vacuum pump of said vacuum base.

In some of the vacuum container systems as described in '591, said extraction airway is in fluid communication through said lid and the walls of said container, wherein said lid comprises said internal outlet and said internal airway portion within said container.

In some of the vacuum container systems as described in '591, said extraction airway is in fluid communication through the walls of said container, wherein said walls comprise said internal outlet and said internal airway within said container.

In some of the vacuum container systems as described in '591, said lid-release button is located at one of:

in the lid of said vacuum container; and on the walls of said vacuum container.

Some of the vacuum container systems as described in '591 further comprise a pump-release button allowing for selected equalization of pressure within said external airway portion, while said check valve retains said internal air chamber vacuum sealed, for facilitating disconnection of said container from said pump under pressurized container conditions.

In some of the vacuum container systems as described in '591, said pump-release button is combined with at least one of: said lid-release button, and said check valve, in a single module.

In some of the vacuum container systems as described in '591, said lid-release button and said check valve are combined in a single module.

In some of the vacuum container systems as described in '591, said air pump is further operational for selectively pumping air back into an external portion of said extraction airway, while said check valve retains said internal air chamber vacuum sealed, for facilitating disconnection of said container from said vacuum pump under pressurized container conditions.

Some of the vacuum container systems as described in '591, further comprise a T-valve in fluid communication with said extraction airway and said pump, for reversing the pump suction direction when pumping air back into said extraction airway.

Sensors 120 (or equivalents) may be incorporated in suitable particular location in the embodiments described in '591, in addition to the general disposition in the container, the lid or the vacuum base, e.g., in the extraction airway, its internal air extraction outlet, its external air extraction outlet, in vicinity of the vacuum pump, or in the suction port.

In alternative embodiments the container may be sealed by an electronic locking mechanism that is disposed in the complementary sealing lid and that is activated by an accompanying triggering transmitter which is installed in the base unit, or other lid locking techniques.

Figure 2:
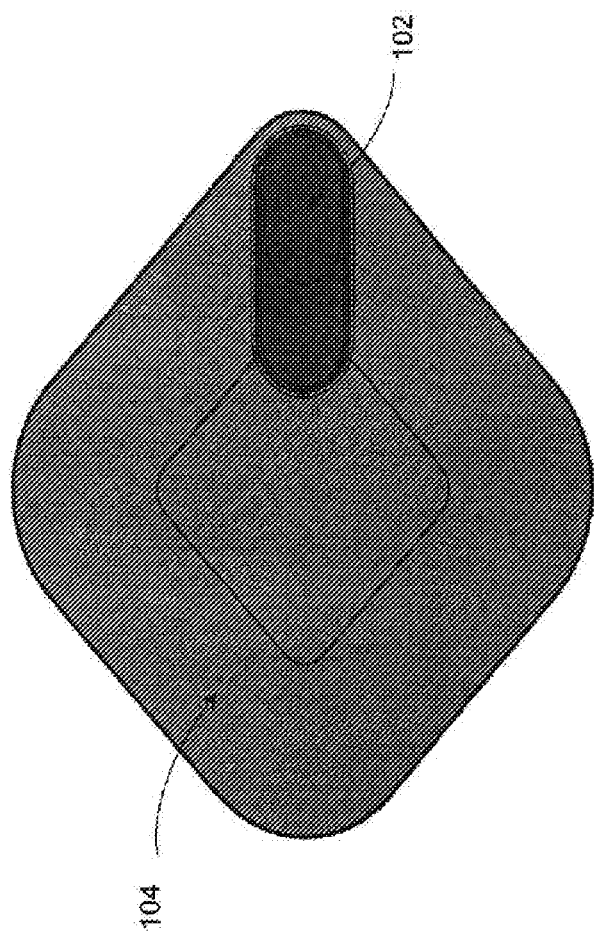
FIG. 2 depicts an embodiment that illustrates a complementary sealing lid.

Reference is now made to FIG. 2—which is an embodiment that illustrates a complementary sealing lid.

Complementary sealing lid 104 incorporates sealing features which conform to the disclosure in '591 and the description above.

Sealing mechanism handle 102 is configured to release a seal which is created when placed upon base unit 108, as described in '591.

3. A base unit

The base unit in various embodiments includes one or more of the following:

a. A weight measurer (e.g., a scale mechanism) for measuring the weight of sealable containers placed thereon.

b. A processing device operational for updating a registry of sealable containers and their inputted content, calculating the weight of the content (the weight of the sealable container is deducted), and logging weight and other collected data including the timestamp of the event (the processing device comprises or references an operationally coupled clock, like most processor units do).

c. A connectivity module allowing the device to connect (e.g., through the internet) and update an external service holding the registry and additional data such as shelf life projections. Alternatively, a local memory capable of holding a registry of sealable containers and their inputted contents, as well as information on projected shelf life for potential stored food items, is used in lieu of the external source. Such a service or memory may be deemed as a tracking entity, which may be useful for presenting the implications of the information derived from the system's readings or user tagged information (see item e. below).

d. A reader capable of identifying the sealable container placed, based on the mechanism used for identification (for example an RFID antenna and a correspondent RFID tag on the container and/or sealing lid, though this can be achieved through other means as noted above).

e. An interface allowing users to "tag" the contents of a sealable container and detect when the contents are changed. This may be achieved through the integration of a voice interface (and its required parts such as microphones) into the base unit. This can also be achieved by the integration of a screen and buttons into the base unit or communicating with an accompanying device (such as a smartphone running an appropriate app.).

f. A vacuum seal inducer for drawing air from the sealable container. For example, a vacuum pump and suction, such as described in '591, or by alternative vacuum seal generation depending on the sealing method used in conjunction with the complementary sealing lid.

g. Freshness sensor(s) similar to sensors 120 discussed above.

Figure 3:
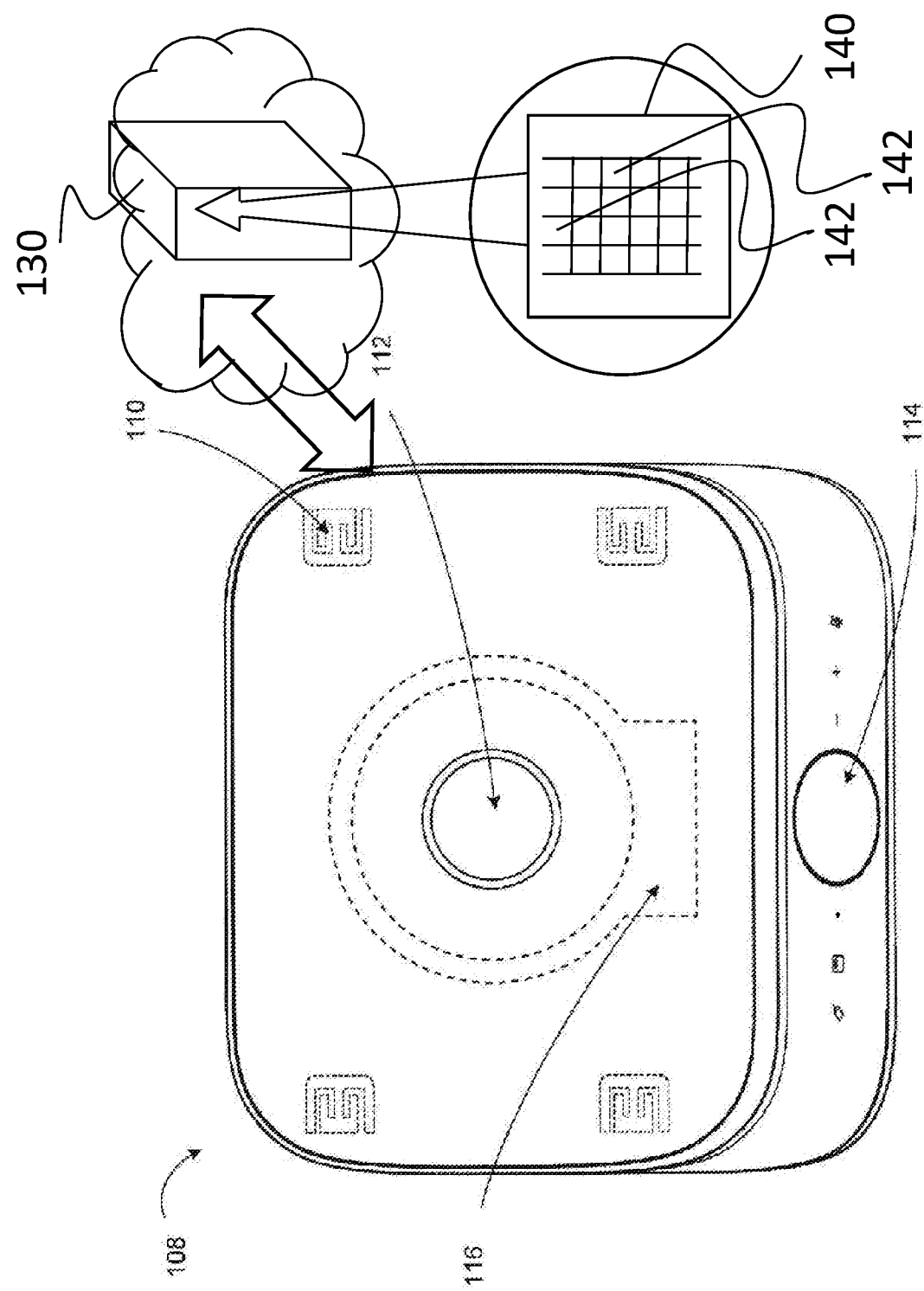
FIG. 3 illustrates an exemplary design for a base unit constructed and operative in accordance with one embodiment.

Reference is now made to FIG. 3 which features an exemplary design for the base unit 108, including: Load cells 110 which are mounted in the four corners of the top of base unit 108, which allow the recording of weight placed atop. Suction port 112 allows the creation of sub-atmospheric pressure inside sealable container 100, and thereby sealing it in accordance with '591. For example, user interface 114 comprises a voice user interface that allows identification of sealable container contents and comprises two front mounted microphone units and a speaker unit. Reader 116 is capable of identifying the sealable container. For example, reader 116 comprises an RFID antenna which can read the RFID tag/chip integrally incorporated in sealable container 100.

As an example, the system can be used at home or in a commercial business. Once a user places food in the sealable container, the user must place the sealable container atop a base unit to seal the sealable container. Upon such placement, data such as the content's weight, and/or freshness/expiration date, is collected and the user may be prompted to (or prompt the unit to) identify the sealable container's contents ("tagging") using the chosen input method, for example by a voice interface. This data is collected by the system's registry and assigned to the specific sealable container.

In one embodiment, the following logic is applied in an attempt to ensure compliance with updating the registry when content is changed: When a sealable container's weight is measured, if it has increased since the last registry input, the system assumes the content has been changed and requests the user to tag the new food entry. In more particular embodiments where the system seals the sealable containers by creating negative pressure, means for measuring freshness of the food item is provided. For example, means comprise at least one pressure sensor as is described immediately below.

the system may include a pressure sensor allowing measuring the amount of time it took to reach a predefined pressure (or vacuum) level, thereby allowing to calculate the volume occupied by the content (this is possible since the identification of the sealable container includes its weight and volume). This can be used in combination with the weight measurement to assess the density of the content, which allows the system to further identify changes to density that may indicate a change of content other than the weight change, such as spoilage.

In similar embodiments having a pressure sensor when the food item is placed in the container, a first amount of time required to reach a predefined sub-atmospheric pressure in the container is stored. The pressure in the container may subsequently, for example just prior to intended use of the food item, or at periodic testing intervals, be allowed to return to ambient atmospheric pressure, and subsequently the air in the container may be pumped out again. Second and following amounts of time required to reach a predefined sub-atmospheric pressure in the container may be compared to the stored first amount of time; accordingly, the system may issue an alert when a difference between the second amount of time and the first amount of time exceed a predetermined value. The system may generate a chart of the time measurements and may issue an alert when the amount of time significantly deviates from a trend in the chart by a predetermined value. In some embodiments the predetermined values may be selected according to the measured or inputted weight of the stored food item.

In some embodiments the user is responsible for updating the system that the food in a container is not fresh and not to add new food to the old food, and accordingly procedurally the old date may remain for all the food in the container, i.e., the oldest food will determine the expiry date for both the old and the new food items. Such option may be useful for example when a small amount of relatively new food items is added to a larger amount of older food items. Optionally, in other embodiments sensor(s) similar to sensor (s) 120 will determine if food is actually spoiled. In some embodiments the system may prevent use of the food that is determined as spoiled, for example by locking the containers which may be opened by an administrator only, but some embodiments may be configured to allow at least some users to override the determination, such as some/all adult users, while other users, e.g., children will not be allowed to open the containers.

The weight of the contents may be calculated by subtracting the known weight of the specific sealable container, or the sealable container type (with such data either held in an external service or a memory in the base), from the measured weight ("auto-tare" weight), and logged in the system. For example, the identifier and weight data are transmitted using a communication module to an external service which logs them into a database having container identifier and weight fields uniquely associated with each other. These actions can also be executed to a local memory, e.g., a memory in the base unit.

In another example, the base unit can also be used as a kitchen scale, to measure amount of food—either in an associated sealable container or separately, or in an unrelated sealable container. Based on the auto-tare feature mentioned above, when placing an associated sealable container, the system will allow users to measure weight without requiring Tare to subtract the sealable container's weight. This set of operations can be used along with the system's interface for assignments such as meal preparation (requiring placement of specific portions of several food items into a sealable container), or as part of a guided cooking program. In some embodiments, the system may include identifiable measuring cups with their weight registered in the system to allow weighing without Tare.

In further embodiments, the system begins tracking a food item from the initial tagging and may generate alerts. For example, in some embodiments, alerts may be sent through an external service, by sending alerts to the user's phone. In other embodiments alerts may be provided through the use of a screen or indicative lights installed in the base unit or any other method of alerting users. Allowed consumption periods of food items that are about to expire, may be based on an estimate of the content's shelf life, either inputted by the external service based on assignment of the registered food to a shelf life expectancy table stored there, or based on a list stored in a memory in the base unit, or the readings of freshness sensor(s). This tracking stops when a new food item is tagged for the sealable container or the alert is otherwise dismissed.

The system creates a new entry each time a sealable container is sealed, allowing tracking of changes to the contents and generation of consumption data.

Figure 4:
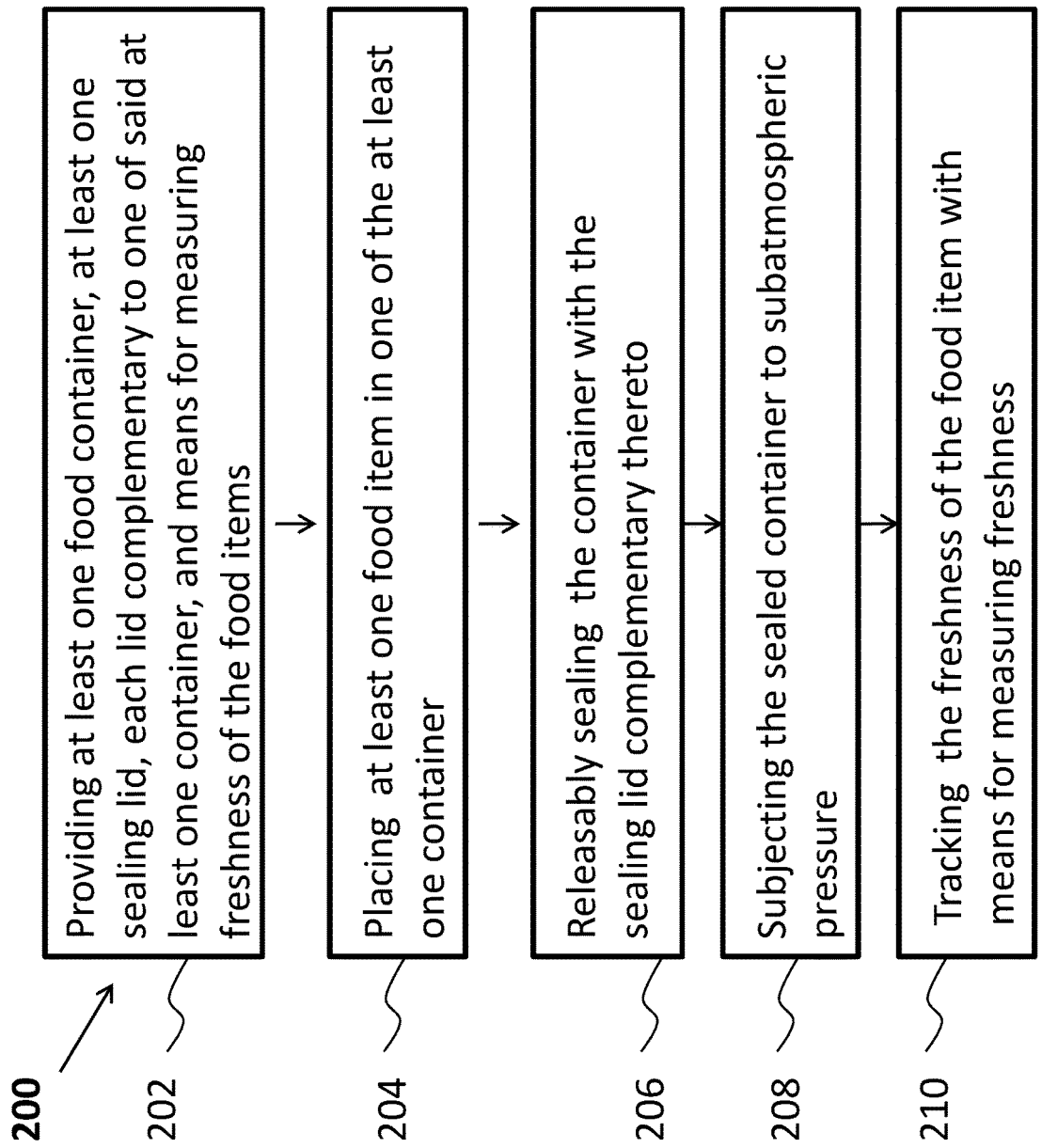
FIG. 4 illustrates a food storing and consumption tracking method.

A food storing and consumption tracking method may be implemented for using system 100. Reference is now made to FIG. 4 which illustrates a food storing and consumption tracking method 200. In step 202 of method 200 at least one food container, at least one sealing lid, each lid complementary to one of said at least one container, and means for measuring freshness of the food items are provided. In step 204 at least one food item is placed in one of the at least one. In step 206, the container with the sealing lid complementary thereto is releasably sealed. Step 208 includes subjecting the sealed container to sub-atmospheric pressure. In step 210, the freshness of the food item is tracked with means for measuring freshness.

In some method embodiments the sealable container may be sealed by the base unit, when closed with the complementary sealing lid and placed on the base unit, in conjunction with reading a unique identifier and measuring the content of the sealable container.

In some method embodiments the sealing may occur only upon engagement of the unsealed sealable container with a base unit.

Some method embodiments further comprise recording, tracking, and/or presenting relevant information respective of the sealable container. The relevant information may be based on the measuring of the content, and/or user tagging in addition or in lieu of the measuring.

This information may be further conveyed to the user for instructing with associated implications (e.g., food is about to run out of freshness is about to expire) and/or further conveyed to a tracking identity, with or without such implications.

The instructing may comprise, for example, to discard the spoiled food or to consume it soon (e.g., within 40 hours) before expiration due to spoilage.

In step 212, the sealable container is stored with its content for further consumption. In step 214, the sealable container after being sealed is opened by opening the complementary sealing lid, which can be opened by releasing the seal (e.g., for consumption or disposal of expired content). User info may be tagged if the sealable container is not required to be resealed thereafter (e.g., content was consumed or disposed of), for avoiding redundant system alerts.

The registry 140 may be located in the servers 130 and/or in the base unit 108. Embodiments wherein the registry 140 is in the base unit 108 (not shown) may allow entering data 142 regarding the containers 100 even when the servers 130 are offline, or even in a system that is not connected/not connectable to the internet/intranet.

In other embodiments the registry is only in the cloud (servers 130), which may simplify and reduce the cost of the base unit 108 and allow replacing/fixing the base unit without concern for continuous local storage of data and not losing them.

In some embodiments wherein both the servers and the base unit contain the registry 140, the registry in the base unit 108 can be a temporary storage of data in between updates to the servers, or as backup to the data in the servers.

Alternatively, the registry 140 in the servers 130 may be a backup for data in the base unit. In some embodiments the system comprises a plurality of base units 108, each situated at a different location. The units may be connected via intranet or internet, to share information for example regarding the availability of adjacent containers 100 when there is a shortage at a certain location.

Data may be manually input into the registry 140, typically by the user, for example via an app and/or a vocal command to the unit 108. In some embodiments a base unit 108 may read from sensors 120 (or equivalent sensor(s)) when a food item is placed inside the container, as identified for example by a detected weight of the container, and according to the reading data may be stored in the registry in association with the container 100, either the raw readings or an output derived from the raw data. For example, the output may be a chemical signature that identifies the food item.

The registry 140 may comprise data or fields 142 such as date of first registry of the container 100 or the container 100 with the current food item, vacuum suction date, weight, moisture, temperature at vacuum (if too high), sensor feedback, and optionally any further added inserted data.

Typically, a new event is initiated as part of the measuring of a container when coupling thereof for vacuum generation, either around the time that a new food item is placed in the container or at time intervals thereafter for example for periodic inspections.

In some embodiments in addition to placing the container and/or lid against the base unit a new event may be initiated by a vocal command to the system, even when the container/lid is not operationally coupled to the base unit.

While certain embodiments of the disclosed subject matter have been described, so as to enable one of skill in the art to practice the present invention, the preceding description is intended to be exemplary only. It should not be used to limit the scope of the disclosed subject matter, which should be determined by reference to the following claims.

Clarifications about Terminology

In the discussion, unless otherwise stated, adjectives such as "substantially" and "about" that modify a condition or relationship characteristic of a feature or features of an embodiment of the invention, are to be understood to mean that the condition or characteristic is defined to within tolerances that are acceptable for operation of the embodiment for an application for which it is intended.

It should be noted that the term "item" as used herein refers to any physically tangible, individually distinguishable unit of packaged or unpackaged good or goods. Positional terms such as "upper", "lower", "right", "left", "bottom", "below", "lowered", "low", "top", "above", "elevated", "high", "vertical" and "horizontal" as well as grammatical variations thereof as may be used herein do not necessarily indicate that, for example, a "bottom" component is below a "top" component, or that a component that is "below" is indeed "below" another component or that a component that is "above" is indeed "above" another component as such directions, components or both may be flipped, rotated, moved in space, placed in a diagonal orientation or position, placed horizontally or vertically, or similarly modified. Accordingly, it will be appreciated that the terms "bottom", "below", "top" and "above" may be used herein for exemplary purposes only, to illustrate the relative positioning or placement of certain components, to indicate a first and a second component or to do both.

"Coupled with" means indirectly or directly "coupled with".

It is important to note that the methods described above are not limited to the corresponding descriptions. For example, the method may include additional or even fewer processes or operations in comparison to what is described herein and/or the accompanying figures. In addition, embodiments of the method are not necessarily limited to the chronological order as illustrated and described herein.

It should be understood that where the claims or specification refer to "a" or "an" element or feature, such reference is not to be construed as there being only one of that element or feature. Hence, reference to "an element" or "at least one element" for instance, may also encompass "one or more elements".

Unless otherwise stated, the use of the expression "and/or" between the last two members of a list of options for selection indicates that a selection of one or more of the listed options is appropriate and may be made.

It is noted that the term "perspective view" as used herein may also refer to an "isometric view" and vice versa.

It should be appreciated that certain features which are, for clarity, described in the context of separate embodiments, may also be provided in combination in a single embodiment. Conversely, various features, which are, for brevity, described in the context of a single embodiment, example and/or option, may also be provided separately or in any suitable sub-combination or as suitable in any other described embodiment. Certain features described in the context of various embodiments are not to be considered essential features of those embodiments, unless the embodiment, example, and/or option are inoperative without those elements. Accordingly, features, structures, characteristics, stages, methods, modules, elements, entities or systems disclosed herein, which are, for clarity, described in the context of separate examples, may also be provided in combination in a single example. Conversely, various features, structures, characteristics, stages, methods, modules, elements, entities or systems disclosed herein, which are, for brevity, described in the context of a single example, may also be provided separately or in any suitable sub-combination.

It is noted that the term "exemplary" is used herein to refer to examples of embodiments and/or implementations, and is not meant to necessarily convey a more desirable use-case.

In alternative and/or other embodiments, additional, fewer, and/or different elements may be used.

Throughout this description, various embodiments may be presented in a range format. It should be understood that the description in range format is merely for convenience and brevity and should not be construed as an inflexible limitation on the scope of the embodiments. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include—where applicable—any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

While the aspects have been described with respect to a limited number of embodiments, these should not be construed as scope limitations, but rather as exemplifications of some of the embodiments.

The invention claimed is:

1. A food storing and tracking system comprising:
   a plurality of food containers, each of the food containers configured to contain at least one food item, each of the food containers comprising a unique identifier;
   a plurality of sealing lids, each sealing lid complementary to a respective one of the food containers;
   a registry, configured to store information relating to the food containers and contents thereof; and
   a base unit comprising:
      a weight measurer, configured to measure a weight of a respective one of the food containers placed on the base unit;
      a reader, configured to identify the respective one of the food containers placed on the base unit by reading the unique identifier thereof;
      an interface, configured for tagging the at least one food item placed in the respective one of the food containers;
      a processor, configured to calculate a weight of the food item contained in the respective one of the food containers by subtracting a known weight of the food container or a container type of the food container from a measured weight, and to log a calculated weight, the processor configured to update the registry with information relating to the respective one of the food containers and contents thereof;
   wherein the sealing lid is configured for releasably sealing the respective one of the food containers upon engagement with the base unit; and
   wherein the system is configured to track a freshness of the food item in the respective one of the food containers, based on projected shelf life information for potential stored food items, and based on updated registry information, and to generate at least one alert relating to the tracked freshness.

2. The food storing and tracking system of claim 1, wherein the respective one of the food containers is configured for releasable sealing upon engagement with the base unit, in conjunction with reading the unique identifier.

3. The food storing and tracking system of claim 1, wherein the base unit further comprises at least one selected from the group consisting of:
   a connectivity module, configured to connect and update an external service, configured to hold at least one of: the registry; and the projected shelf life information for potential stored food items, a local memory, configured to hold at least one of: the registry; and the projected shelf life information for potential stored food items.

4. The food storing and tracking system of claim 1, wherein the base unit comprises a vacuum seal inducer, configured to draw air from the food container through a suction port, to create sub-atmospheric pressure inside the food container.

5. The food storing and tracking system of claim 1, wherein the interface comprises a voice interface.

6. The food storing and tracking system of claim 1, wherein the reader comprises an RFID antenna, configured to detect the unique identifier in the form of a correspondent RFID tag of at least one of the food container and the sealing lid.

7. The food storing and tracking system of claim 1, wherein the registry comprises information selected from the group consisting of: a date of first registry of the container with a current food item; vacuum suction date; weight; moisture; temperature; and sensor feedback of a sensor of the food container.

8. A method for storing and tracking food items, the method comprising the steps of:
   inserting at least one food item into a food container of a plurality of food containers, each food container comprising a unique identifier;
   placing the food container onto a base unit, and releasably sealing the food container with a sealing lid complementary to the food container, upon engagement with the base unit;
   tagging the food item placed in the food container, using an interface of the base unit;

identifying the food container placed on the base unit by reading the unique identifier of the food container, using a reader of the base unit;

measuring a weight of the food container placed on the base unit, using a weight measurer of the base unit;

calculating a weight of the food item contained in the food container by subtracting a known weight of the food container or a container type of the food container from the measured weight, and logging a calculated weight;

updating a registry with information relating to the food container and contents thereof; and tracking a freshness of the food item in the food container, based on projected shelf life information for potential stored food items, and based on updated registry information, and generating at least one alert relating to the tracked freshness.

9. The method of claim 8, wherein at least one of: the registry; and the projected shelf life information for potential stored food items, is held in an external service, accessible by a connectivity module of the base unit.

10. The method of claim 8, further comprising the step of creating sub-atmospheric pressure inside the food container by drawing air from the food container through a suction port using a vacuum seal inducer of the base unit.

11. The method of claim 8, wherein tagging the food item using an interface comprises tagging using a voice interface.

12. The method of claim 8, wherein identifying the food container placed on the base unit comprises using an RFID antenna of the reader to detect the unique identifier in the form of a correspondent RFID tag of at least one of the food container and the sealing lid.

13. The method of claim 8, wherein the registry comprises information selected from the group consisting of: a date of first registry of the food container with a current food item; vacuum suction date; weight; moisture; temperature; and sensor feedback of a sensor of the food container.

* * * * *